United States Patent
Scopton et al.

(10) Patent No.: US 8,088,139 B2
(45) Date of Patent: Jan. 3, 2012

(54) ENDOSCOPIC TISSUE STABILIZATION DEVICE AND RELATED METHODS OF USE

(75) Inventors: Paul Scopton, Winchester, MA (US); Yem Chin, Burlington, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 695 days.

(21) Appl. No.: 11/058,167

(22) Filed: Feb. 16, 2005

(65) Prior Publication Data

US 2005/0182438 A1 Aug. 18, 2005

Related U.S. Application Data

(60) Provisional application No. 60/544,350, filed on Feb. 17, 2004.

(51) Int. Cl.
*A61M 29/00* (2006.01)
(52) U.S. Cl. .......................................... 606/192
(58) Field of Classification Search .......... 606/191–199; 600/184–246
See application file for complete search history.

(56) References Cited

U.S. PATENT DOCUMENTS

| | | | |
|---|---|---|---|
| 3,774,596 A * | 11/1973 | Cook | 600/184 |
| 4,224,929 A | 9/1980 | Furihata et al. | |
| 4,447,227 A | 5/1984 | Kotsanis et al. | |
| 6,142,931 A | 11/2000 | Kaji et al. | |
| 6,277,065 B1 | 8/2001 | Donofrio | |
| 6,706,064 B1 * | 3/2004 | Anson | 623/1.25 |
| 2002/0013601 A1 * | 1/2002 | Nobles et al. | 606/193 |
| 2002/0095150 A1 | 7/2002 | Goble | |
| 2003/0199731 A1 | 10/2003 | Silverman et al. | |
| 2003/0199737 A1 | 10/2003 | Deslauriers et al. | |

* cited by examiner

*Primary Examiner* — Melanie Tyson
(74) *Attorney, Agent, or Firm* — Finnegan Henderson Farabow Garrett & Dunner, L.L.P.

(57) ABSTRACT

Embodiments of the invention include a sleeve for use in a body lumen defined by body tissue. The sleeve includes a collapsible wall defining a lumen and including an inflatable member configured to increase a volume of the lumen when the inflatable member is in an inflated state, a conduit configured to inflate the inflatable member, and a port defined by the collapsible wall and in flow communication with the lumen.

34 Claims, 2 Drawing Sheets

ENDOSCOPIC TISSUE STABILIZATION DEVICE AND RELATED METHODS OF USE

CROSS-REFERENCE TO RELATED APPLICATIONS

This application claims the benefits of priority under 35 U.S.C. §§119(e), 120 to U.S. Provisional Patent Application No. 60/544,350, filed Feb. 17, 2004, the entirety of which is incorporated herein by reference.

DESCRIPTION OF THE INVENTION

1. Field of the Invention

Embodiments of the invention include a sleeve for use in a body lumen defined by body tissue. The sleeve includes a collapsible wall defining a lumen and including an inflatable member configured to increase a volume of the lumen when the inflatable member is in an inflated state, a conduit configured to inflate the inflatable member, and a port defined by the collapsible wall and in flow communication with the lumen.

2. Background of the Invention

Endoscopic methods are commonly used for diagnosis and/or treatment of the gastrointestinal tract. For example, there are several methods of treating esophageal cancer known as endoscopic mucosal resection. Endoscopic mucosal resection may include snaring and then excising sessile adenomas (i.e., tumors attached to a bodily surface) in the esophageal tract. If the adenoma is flat against the esophageal tract, thus making it difficult to snare and excise, one of several methods may be used to raise the flat adenoma so that it may be snared and excised. One method includes using forceps to raise the flat adenoma. Another method includes using a vacuum to raise the flat adenoma. A further method includes injecting saline into the submucosa so as to raise the flat adenoma. If, during saline injection, it is determined that the adenoma is attached to multiple esophageal layers, additional methods may be required to remove the adenoma.

The aforementioned methods and other endoscopic methods requiring access to tissue within the gastrointestinal tract, while effective, have certain drawbacks. For example, due to the tissue folds and constricted space in some portions of the gastrointestinal tract, including the esophagus, it may be difficult to identify, stabilize, access, and/or excise tissue even with the use of an endoscope, especially if tissue such as an adenoma is attached to multiple esophageal layers.

SUMMARY OF THE INVENTION

In accordance with the invention, an embodiment includes a sleeve for use in a body lumen defined by body tissue. The sleeve includes a collapsible wall defining a lumen and including an inflatable member configured to increase a volume of the lumen when the inflatable member is in an inflated state, a conduit configured to inflate the inflatable member, and a port defined by the collapsible wall and in flow communication with the lumen.

Various embodiments of the invention may include any or all of the following features. When the inflatable member is in the inflated state, the sleeve may be configured to substantially stabilize the body tissue defining the body lumen. A non-inflating reinforcing member may be configured to support the collapsible wall. An embodiment may include alternating inflatable members and non-inflatable reinforcing members. A plurality of non-inflating reinforcing members may be arrange about an axis of the sleeve. The plurality of non-inflating reinforcing members may be spaced apart from each other. The collapsible wall may define an open proximal end. The collapsible wall may define an open distal end. A substantially planar portion of the collapsible wall may define the port. A curved portion of the collapsible wall defines the port. The inflatable member may include a plurality of longitudinal channels interconnected by at least one circumferential channel. The inflatable member may include at least one circumferential channel. The inflatable member may include at least one longitudinal channel. The inflatable member may include a plurality of circumferential channels interconnected by at least one longitudinal channel.

Another embodiment of the invention includes a method of substantially stabilizing body tissue defining a body lumen. The method includes providing a sleeve including a collapsible wall defining a lumen and including an inflatable member configured to increase a volume of the lumen when the inflatable member is in an inflated state, the sleeve further including a conduit configured to inflate the inflatable member and a port defined by the collapsible wall and in flow communication with the lumen, advancing the sleeve into the body lumen in a collapsed configuration, and expanding the sleeve so as to exert pressure on and thereby substantially stabilize body tissue defining the body lumen.

Various embodiments of the invention may include any or all of the following features. Expanding the sleeve may include providing fluid to the inflatable member via the conduit. Orienting the sleeve in the body lumen to position the port over a desired portion of body tissue. Advancing the sleeve may include advancing the sleeve through a working channel of an endoscope. The inflatable member may include a plurality of longitudinal channels interconnected by at least one circumferential channel. The inflatable member may include at least one circumferential channel. The inflatable member may include at least one longitudinal channel. The inflatable member may include a plurality of circumferential channels interconnected by at least one longitudinal channel. The sleeve may includes a non-inflating reinforcing member configured to support the collapsible wall. The sleeve may include alternating inflatable members and non-inflatable reinforcing members. The sleeve may include a plurality of non-inflating reinforcing members arranged about an axis of the sleeve. The plurality of non-inflating reinforcing members may be spaced apart from each other.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the exemplary embodiments of the invention, examples of which are illustrated in the specification and accompanying drawings. Wherever possible, the same reference numbers will be used throughout the specification and drawings to refer to the same or like parts.

Figure 1:
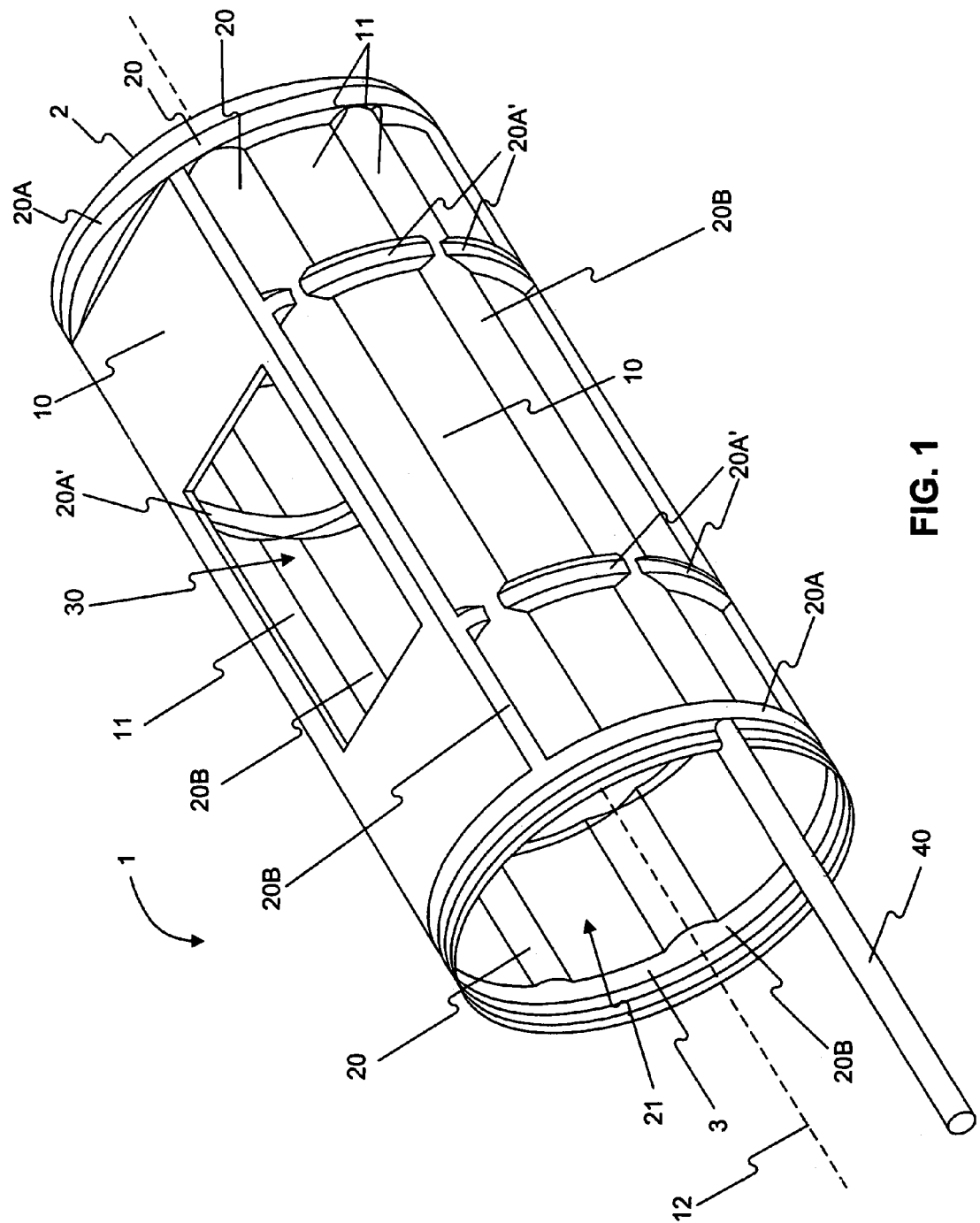
FIG. 1 is a perspective view of an endoscopic device according to an embodiment of the invention.

FIG. 1 depicts an exemplary embodiment of a sleeve. The sleeve 1 may be used with an endoscope and/or one or more endoscopic devices in a medical procedure such as endoscopic mucosal resection, or any other suitable endoscopic or non-endoscopic procedure. The sleeve 1 may include at least one wall 10, at least one inflatable member 20, at least one port 30, and at least one conduit 40.

The at least one wall 10 may be configured to collapse and/or fold, for example, when external pressure is exerted on the wall, in the absence of supporting structures for the wall, and/or when inflatable members of device 1 (to be described herein) are in an uninflated state. The sleeve 1 will be in a collapsed, or contracted, state during its introduction to a tissue site. For example, sleeve 1 will be collapsed when introduced through a working channel of an endoscope. The wall 10 may be made from a flexible polymer material or any other suitable, collapsible, and/or biocompatible material known in the art.

The wall 10 may be reinforced using any method or structure known in the art. For example, relatively rigid reinforcing members 11 made of any suitable material (e.g., metal, polymer) may be disposed in the wall 10 so as to support the wall 10. In FIG. 1, the reinforcing members 11 are coaxial with the longitudinal axis 12 of the sleeve 1 so as to reduce and/or prevent the bending of the wall 10 and/or sleeve 1 in a desired direction, for example, in the longitudinal direction. However, the reinforcing members 11 may be disposed in, or make up part of, any other suitable orientation on the sleeve 1 and/or wall 10 that permits wall 10 to collapse and expand, and may have any desired dimensions, so as to reduce and/or prevent the bending of the wall in any desired direction and/or amount. Thus, in the configuration depicted in FIG. 1, the wall 10 would collapse between the reinforcing members 11.

The at least one inflatable member, or channel, 20 may be configured to inflate and/or become relatively rigid with the introduction of materials (e.g., gas(es), and/or liquid(s)) into the inflatable member 20. The inflatable member 20 may be made of substantially the same material as the wall 10, or may be made from a different suitable material. In the uninflated state, the inflatable member 20 may be configured to collapse.

FIG. 1 depicts inflatable members 20 integrated with the wall 10. Some of the members 20A may be disposed around a central lumen 21 and/or longitudinal axis 12 of sleeve 1, and substantially form circles in their inflated state. In particular, sleeve 1 includes a substantially circular member 20A at each of a proximal most end and a distal most end of sleeve 1. Sleeve 1 also includes inflatable members 20A' along intermediate portions of sleeve 12 (i.e., non-proximal most and non-distal most portions of sleeve 12). Members 20A' have portions similar to substantially circular members 20A, however, members 20A' may not extend fully around the sleeve 12 so as to form a complete circle. Ends of member 20A' may be integrated with other portions of members 20, for example, members 20B as will be described below.

Other members 20B may be parallel to the longitudinal axis 12 and/or reinforcing members 11 so as to expand the sleeve 1 in the longitudinal direction and/or provide support for the sleeve 1. In the sleeve of FIG. 1, members 20B alternate with reinforcing members 11 about the circumference of sleeve 1. At least some of the inflatable members 20 may be in flow communication with each other. For example, as shown in FIG. 1, the circular inflation members 20A and 20A' may be in flow communication with the longitudinal inflation members 20B and thereby in flow communication with one another. However, the inflatable members 20 may also be divided into one or more discrete inflation systems that are not in flow communication with each other.

The inflatable members 20, or at least the material defining the inflatable members 20, may be discrete from the wall 10 and instead be connected to the wall 10 using any method known in the art, for example, adhesives. The inflatable members 10 may also be disposed at any orientation with respect to the wall, and may have any desired geometric configuration. When inflated, the inflatable members 20 may cause the wall 10 to substantially flatten and/or unfold (i.e., form a substantially wrinkle-free surface).

The at least one conduit 40 may be connected to wall 10 and/or inflatable members 20. The conduit 40 may be made out of the same material as the wall 10 and/or inflatable members 20 as set forth above, or it may be made from a different material known in the art. The conduit 40 may be flexible and/or collapsible and sufficiently long to extend from a tissue site within a gastrointestinal tract, through tortuous anatomy, and external to the patient.

The conduit 40 may be in fluid communication with the inflatable members 20 so as to supply materials (e.g., gas(es), and/or liquid(s)) from a materials source to the interior of the inflatable members 20 and cause the inflatable members 20 to inflate. The conduit 40 may be directly connected to at least one of the inflatable members 20 and otherwise in fluid communication with all of the inflatable members 20. In FIG. 1, the conduit 40 is integrated with the wall 10 at the proximal end of sleeve 1. The conduit 40 may be connected to the sleeve 1 using any connection known in the art. At its proximal end, the conduit 40 may be connected to an actuator and a materials supply source configured to control the flow of materials to and/or from the sleeve 1 so as to control the inflation and/or deflation of the sleeve 1.

Wall 10 defines at least one port 30. In FIG. 1, the port 30 is disposed on a center portion of one side of the wall 10 of sleeve 1 and is substantially disposed between at least two inflatable members 20A and at least two inflatable members 20B. However, the port 30 may be disposed on other portions of sleeve 1 and may have a portion that traverses an inflatable member 20.

The port 30 may have any desired shape, dimensions and/or configuration depending on several factors, among them the desired tissue tract area to access and the size of the endoscopic devices that may be advanced to or through the port. For example, as shown in FIG. 1 the port 30 has a substantially flat and/or planar configuration due to the substantially planar portion of wall 10 defining port 30.

The port 30 may also be configured so as to allow an endoscopic tool to draw tissue from the gastrointestinal tract into the central lumen 12 via the port 30, for example, using forceps or suction. Once the tissue is disposed in the central lumen 12, various endoscopic tools known in the art may be used to perform therapy and/or diagnosis on the tissue.

The sleeve 1 and/or any of the aforementioned portions of the sleeve 1 may have any desired shape, dimension and/or configuration dependent on, for example, its deployment location. For example, the sleeve 1 may be curved if the sleeve 1 is to be deployed in a portion of the gastrointestinal tract where a bend may be necessary. In another example, the sleeve 1 may have a substantially D-shaped or oval cross-section.

The distal end 2 of the sleeve 1 may be sealed, for example, to prevent materials from entering the central lumen 12 via the distal end 2 of the sleeve 1. The proximal end 3 may also or alternatively be sealed, for example, in conjunction with the endoscope. If both the proximal end 3 and distal end 2 are sealed, the proximal end 3 may be connected to a vacuum source and a vacuum may be generated in the central lumen 12 of the sleeve 1 so as to allow tissue from the gastrointestinal tract to be vacuumed into the central lumen 12 of the sleeve 1 via the port 30.

At least one endoscopic tool may be used in conjunction with the sleeve. For example, the endoscopic tool may include a forceps, a biopsy forceps jaw, an aspirator, an irrigator, a scissors-like devices, a knife, a cutter, an electrocautery device, a needle, a snare, a basket, and any other endoscopic tool known in the art. The endoscopic tool may be disposed in the central lumen 21 or may be disposed external to the sleeve. The endoscopic tool may be advanced through the same endoscope and/or endoscope channel as the sleeve 1, or the endoscopic tool may be advanced into the gastrointestinal tract independently of the sleeve 1. For example, the endoscopic tool may be exterior and/or cross-parallel to the endoscope. The central lumen 21 may include one or more tool guiding channels configured to guide the endoscopic tool to a desired portion of the sleeve 1, for example, port 30 and/or tissue extending into the central lumen 21 via port 30. The tool guiding channels may also be configured to guide the endoscopic tool out of the sleeve 1, for example, through port 30, the opening on the proximal end 3 of the sleeve 1, and/or the opening on the distal end 2 of the sleeve 1.

The endoscopic tool used in conjunction with the sleeve 1 may be a cutter, such as a snare, configured to cut tissue, for example, from the walls of the gastrointestinal tract. The tissue may be cut by extending the cutter to or through the port 30. The tissue may be cut by first drawing tissue into the central lumen 12 through the port and then cutting the tissue.

The sleeve 1 may include a pouch or other storage portion configured to retrieve and store tissue samples acquired, for example, using the aforementioned cutter. The pouch may be disposed on any portion of the sleeve 1. For example, the pouch may be on the wall 10 and/or inflatable member 20, and may be disposed on an internal and/or external portion of the sleeve 1. The pouch may be integrated with portions of the sleeve 1, or the pouch may be manufactured separately from the sleeve 1 and then attached to the sleeve 1, for example, using adhesives.

The sleeve 1 may include a portion for performing electrocautery, for example, at least one cautery wire. The cautery wire may be disposed on an external portion of and/or embedded in one or more of the wall 10, inflatable member 20, and conduit 40 in any desired shape, orientation, and/or configuration. The cautery wire may be connected to an electrical power source external to the patient through suitable leads or other wires. The cautery wire may be configured to cauterize a portion of the tissue wall defining the gastrointestinal tract that the cautery wire comes into contact with.

One or more portions of the sleeve 1 may have a desired drug coating. For example, external portions of the wall 10 may be coated with a drug so that the wall 10, for example when inflated, may deliver drugs to a portion of the tissue defining the gastrointestinal tract. Alternatively or in combination with a drug coating, sleeve 1 may include a coating of any other desired therapeutic or diagnostic agent.

The sleeve 1 may have one or more conduits, in addition to conduit 40, connected to sleeve 1 and extending proximally to the exterior of the patient. The conduit may be disposed within the central lumen 12, walls 10, and/or inflatable members 20. The conduit may be disposed external to the sleeve 1. The conduit may be configured to deliver materials (e.g., gas(es), and/or liquid(s)) to one or more portions of the sleeve 1 and/or portions of the gastrointestinal tract so as to flush the one or more portions of the sleeve 1 and/or portions of the gastrointestinal tract. The conduit may be configured to remove materials (e.g., gas(es), and/or liquid(s)) from one or more portions of the sleeve 1 and/or portions of the gastrointestinal tract.

Figure 2:
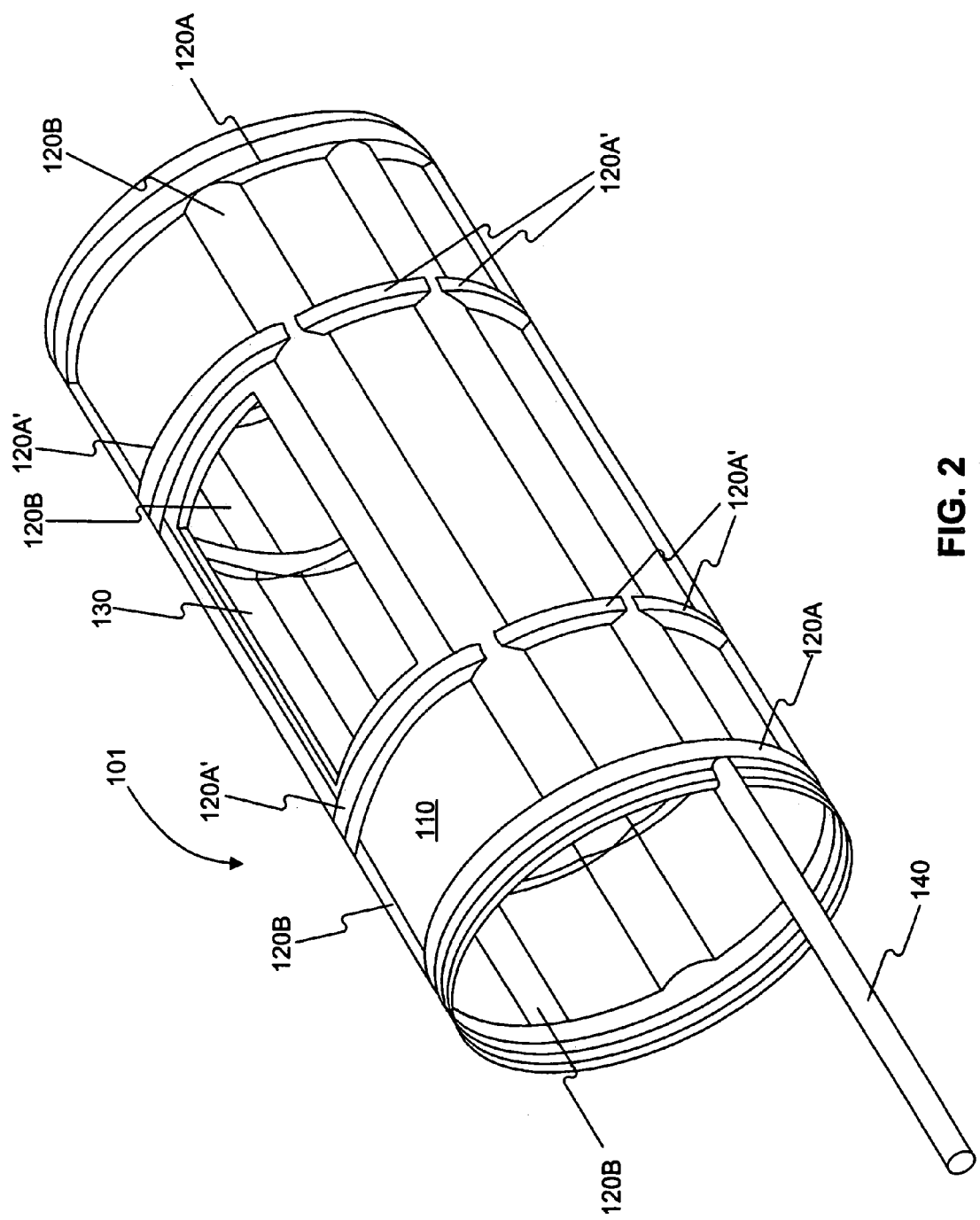
FIG. 2 is a perspective view of an endoscopic device according to another embodiment of the invention.

FIG. 2 shows another embodiment of a sleeve 101 according to the invention. The configuration of the sleeve 101 in FIG. 2 is substantially similar to the configuration of the sleeve 1 in FIG. 1, except for the following differences. As shown in FIG. 2, the port 130 may have a rounded and/or curved configuration due to the substantially rounded or curved portion of wall 110 defining port 130. The sleeve 101 may also have inflation channels 120A' running substantially adjacent to the proximal and distal edges of the port 130, for example, to add rigidity to the port 130. Various inflation channels 120A' may combine to form an inflation channel similar to inflations channels 120A, with a difference being that the inflation channels 120A' are on an intermediate portion of the sleeve 101. Ends of the inflation channels 120A' adjacent the port 130 may be integrated with inflation channels 120B. The inflation channels 120, 120A, 120A', 120B may be in flow communication with at least one conduit 140.

Embodiments of the invention include methods of using a sleeve including any or all of the aspects set forth above. For example, the method may include providing the sleeve 1 in a collapsed configuration (i.e., the walls 10 and/or inflatable members 20 are collapsed and not inflated), and then advancing the sleeve 1 into the gastrointestinal tract using any method known in the art. In some embodiments, the sleeve 1 may be advanced through a working channel of an endoscope, however, in other embodiments the sleeve 1 may be advanced into the gastrointestinal tract independently of an endoscope. The reinforcing members 11 may provide sufficient structural support to sleeve 1 to prevent the sleeve 1 from knotting, tangling, and/or twisting to a degree that does not permit the wall 10 and inflatable members 20 to properly inflate once it is positioned in the desired portion of the gastrointestinal tract.

When the sleeve 1 has been advanced to the desired portion of the gastrointestinal tract, for example, the portion of the gastrointestinal tract having an adenoma, the sleeve 1 may be positioned so that the port 30 is adjacent the portion of the gastrointestinal tract where therapy or diagnosis is desired. Proper positioning may be achieved through any suitable imaging method, including use of the optics of an endoscope.

Materials (e.g., gas(es), and/or liquid(s)) from a materials source may then be advanced through conduit 40 into at least one inflatable member 20 so as to inflate the at least one inflatable member 20. As the inflatable member 20 inflates, the volume of the central lumen 21 of the sleeve 1 expands due to the uncollapsing, expansion, and/or straightening of the wall 10. As the sleeve 1 expands, the walls 10 and/or inflatable members 20 come into contact with, and exert pressure on, the walls of gastrointestinal tract and cause it to expand. During this expanding of the walls of the gastrointestinal tract, the volume of the desired portion of the gastrointestinal tract is increased, the folds of the tract walls are smoothed out, and/or the desired portion of the gastrointestinal tract is visible, stabilized, accessible, and/or enters the central lumen 21 through the port 30. Once inflated, the sleeve 1 forms a substantially rigid structure within the gastrointestinal tract. During or after inflation of the sleeve 1, the position of the port 30 may be adjusted as desired. For example, if initial positioning does not permit access to the desired tissue, sleeve 1 can be fully or partially uninflated and repositioned. Once the port 30 is properly positioned, the port 30 may be used to permit access to the desired portion of the gastrointestinal tract for therapy and/or diagnosis.

Various types of therapy may be conducted on the desired tissue portion of the gastrointestinal tract via the walls 10, port 30, open distal end 2, and/or open proximal end 3, some exemplary embodiments of which are set forth below.

If the distal end 2 and the proximal end 3 of the sleeve 1 are sealed, the port 30 may be placed substantially flush with the desired tissue portion of the gastrointestinal tract, and then a vacuum source connected to the central lumen 21 of the sleeve 1 may be activated. Once activated, the desired tissue portion may be aspirated into the central lumen 21 through the port 30, and then therapy may be performed on the desired tissue portion.

If the distal end 2 and the proximal end 3 of the sleeve 1 are not sealed, the port 30 may be placed substantially flush with the desired tissue portion of the gastrointestinal tract, and then the desired tissue portion may be drawn into the central lumen 21 via the port 30 using a suitable medical device, for example forceps or a separate suction device placed proximate port 30.

The desired tissue portion may be cut from the gastrointestinal tract. The desired tissue portion may be cut using a cutter known in the art, such as a snare or a biopsy forceps jaw. The cutter may be advanced through the central lumen 21 and to or out of the port 30. The cutter, or other endoscopic tool, may be advanced to or out of the port 30 (or other desired portion of sleeve 1) via a tool guiding channel. Once cut, the tissue portion may be disposed in the central lumen 21 and then aspirated out of the sleeve 1 via a device connected to the central lumen 21, for example, a vacuum device. In the alternative, the tissue portion may be placed in a pouch connected to and/or integrally formed with, or separate from, the sleeve 1. As a further alternative, the tissue may be removed via the closed jaws of a biopsy forceps jaw assembly.

The desired tissue portion, and other portions of the gastrointestinal tract, may be flushed and/or irrigated with materials (e.g., gas(es), and/or liquid(s)) so as to, for example, clear obstructions from the desired tissue portion. The materials may be delivered via a conduit disposed in the central lumen 21 of sleeve 1, via the central lumen 21 itself, a conduit integrated with the sleeve 1, and/or a conduit disposed external to the sleeve 1.

The desired tissue portion, and other portions of the gastrointestinal tract, may have materials removed so as to, for example, clear obstructions from the desired tissue portion. The materials may be removed via a conduit disposed in the central lumen 21 of sleeve 1, via the central lumen 21 itself, a conduit integrated with the sleeve 1, and/or a conduit disposed external to the sleeve 1. The conduit may be connected to a suitable vacuum source known in the art.

If drugs or other therapeutic or diagnostic agents are coated on a portion of the sleeve 1, such as the walls 10, then the sleeve 1 may be used to deliver drugs or agents to the desired tissue portions of the gastrointestinal tract so as to conduct chemical therapy on the desired tissue portions. The sleeve 1 may be configured to apply the drug or agent evenly over the desired tissue portion when the sleeve 1 is substantially in its fully inflated configuration.

If cautery wires are embedded in the sleeve 1, the sleeve 1 may be used to cauterize portions of the gastrointestinal tract, for example, by providing electricity to the cautery wires. Electrocautery may be applied, for example, after severing tissue from the tract.

Once the desired therapy has been completed, the sleeve 1 may be deflated by removing materials from the inflatable member 20 via the conduit 40 or another opening using any method known in the art (e.g., opening a valve, puncturing a hole, and/or creating a vacuum). During the removal of the materials, the inflatable member 20 and/or wall 10 may collapse, and then the sleeve 1 may be removed from the gastrointestinal tract using any method known in the art, such as retraction through the working channel of an endoscope.

The devices and methods set forth above may be used in any medical or non-medical procedure. For example, while the devices and methods set forth above are disclosed as being used in treating the gastrointestinal tract, they may also be used to treat any body lumen or organ.

Any of the various aspects set forth in any of the embodiments may be used in conjunction with any other aspect set forth in any of the embodiments. For example, more than one sleeve 1 may be advanced into the gastrointestinal tract. Moreover, aspects may be removed from embodiments if desired.

The sleeve 1 may have any desired dimensions, orientation, and/or configuration, for example, dimensions, orientation, and/or configuration that correspond to a particular portion of the gastrointestinal tract.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A sleeve for use in a body lumen defined by body tissue, comprising:
    a collapsible wall defining a lumen and including a plurality of longitudinal, non-inflating members and an inflatable member including a plurality of longitudinal, inflatable portions and configured to increase a volume of the lumen when the inflatable member is in an inflated state, wherein the plurality of longitudinal, inflatable portions alternate with the plurality of longitudinal, non-inflating members about a circumference of the collapsible wall, the collapsible wall defining a proximal end having a first substantially circular outer periphery and a distal end having a second substantially circular outer periphery;
    a conduit configured to inflate the inflatable member; and
    a port defined by the collapsible wall and in flow communication with the lumen, wherein the port is disposed in a substantially planar wall that is uninflatable and is recessed within the first and second outer peripheries, and wherein the substantially planar wall is disposed in a plane that is substantially parallel to a longitudinal axis of the lumen.

2. The sleeve of claim 1, wherein when the inflatable member is in the inflated state, the sleeve is configured to substantially stabilize the body tissue defining the body lumen.

3. The sleeve of claim 1, wherein the plurality of longitudinal, non-inflating members include a plurality of non-inflating reinforcing members configured to support the collapsible wall.

4. The sleeve of claim 3, wherein the plurality of non-inflating reinforcing members are arranged about an axis of the sleeve.

5. The sleeve of claim 4, wherein the plurality of non-inflating reinforcing members are spaced apart from each other.

6. The sleeve of claim 1, wherein the proximal end defined by the collapsible wall is open.

7. The sleeve of claim 1, wherein the distal end defined by the collapsible wall is open.

8. The sleeve of claim 1, wherein the plurality of longitudinal, inflatable portions are interconnected by at least one circumferential channel.

9. The sleeve of claim 1, wherein the inflatable member includes at least one circumferential channel.

10. The sleeve of claim 1, wherein the inflatable member includes a plurality of circumferential channels interconnected by at least one of the plurality of longitudinal, inflatable portions.

11. The sleeve of claim 1, wherein the sleeve further includes a cautery wire.

12. The sleeve of claim 1, wherein a portion of the sleeve includes a drug coating.

13. The sleeve of claim 1, wherein the sleeve further includes a storage portion.

14. The sleeve of claim 1, wherein the proximal end is adapted to be connected to a vacuum source.

15. The sleeve of claim 1, wherein the sleeve consists of only one port.

16. The sleeve of claim 1, wherein the sleeve further includes an inflatable portion extending radially away from a reinforcement member.

17. The sleeve of claim 1, wherein the inflatable member includes a first inflatable member defining the first substantially circular outer periphery and being the proximal most inflatable member on the sleeve, a second inflatable member defining the second substantially circular outer periphery and being the distal most inflatable member on the sleeve, and a third inflatable member between the first and second inflatable members, and wherein an outer diameter of the second substantially circular outer periphery is substantially the same as an outer diameter of the third inflatable member.

18. The sleeve of claim 17, wherein an outer diameter of the first substantially circular outer periphery is substantially the same as the outer diameter of the third inflatable member.

19. The sleeve of claim 17, wherein the third inflatable member extends only partially around the sleeve.

20. A sleeve for use in a body lumen defined by body tissue, comprising:
a collapsible wall defining a lumen and including a plurality of longitudinal, non-inflating members and an inflatable member including a plurality of longitudinal, inflatable portions and configured to increase a volume of the lumen when the inflatable member is in an inflated state, wherein the plurality of longitudinal, inflatable portions alternate with the plurality of longitudinal, non-inflating members about a circumference of the collapsible wall;
a conduit configured to inflate the inflatable member; and
a port defined by the collapsible wall and in flow communication with the lumen, wherein the port is disposed in a substantially planar wall, the substantially planar wall being uninflatable and disposed in a plane that is substantially parallel to a longitudinal axis of the lumen.

21. The sleeve of claim 20, wherein when the inflatable member is in the inflated state, the sleeve is configured to substantially stabilize the body tissue defining the body lumen.

22. The sleeve of claim 20, wherein the plurality of longitudinal, non-inflating members include a plurality of non-inflating reinforcing members configured to support the collapsible wall.

23. The sleeve of claim 20, wherein the sleeve further includes one of a cautery wire, drug coating, or storage portion.

24. The sleeve of claim 20, wherein the sleeve further includes an inflatable portion extending radially away from a reinforcement member.

25. The sleeve of claim 20, wherein the inflatable member includes a first inflatable member defining a first outer diameter and being the proximal most inflatable member on the sleeve, a second inflatable member defining a second outer diameter and being the distal most inflatable member on the sleeve, and a third inflatable member defining a third outer diameter between the first and second inflatable members, and wherein the second outer diameter is substantially the same as the third outer diameter.

26. The sleeve of claim 25, wherein the first outer diameter is substantially the same as the third outer diameter.

27. The sleeve of claim 25, wherein the third inflatable member extends only partially around the sleeve.

28. A sleeve for use in a body lumen defined by body tissue, comprising:
a collapsible wall defining a lumen and including a plurality of longitudinal, non-inflating members, a plurality of longitudinal, inflatable portions, a first inflatable member, a second inflatable member, and a third inflatable member configured to increase a volume of the lumen when the inflatable members are in an inflated state, the first inflatable member defining a first outer diameter and being the proximal most inflatable member on the sleeve, the second inflatable member defining a second outer diameter and being the distal most inflatable member on the sleeve, the third inflatable member defining a third outer diameter between the first and second inflatable members, wherein the second outer diameter is substantially the same as the third outer diameter, and wherein the plurality of longitudinal inflatable portions alternate with the plurality of longitudinal, non-inflating members about a circumference of the collapsible wall;
a conduit configured to inflate the inflatable members; and
a port defined on an uninflatable portion of the collapsible wall and in flow communication with the lumen.

29. The sleeve of claim 28, wherein when the inflatable members are in the inflated state, the sleeve is configured to substantially stabilize the body tissue defining the body lumen.

30. The sleeve of claim 28, wherein the plurality of longitudinal, non-inflating members include a plurality of non-inflating reinforcing members configured to support the collapsible wall.

31. The sleeve of claim 28, wherein the sleeve further includes one of a cautery wire, drug coating, or storage portion.

32. The sleeve of claim 28, wherein the sleeve further includes an inflatable portion extending radially away from a reinforcement member.

33. The sleeve of claim 28, wherein the first outer diameter is substantially the same as the third outer diameter.

34. The sleeve of claim 28, wherein the third inflatable member extends only partially around the sleeve.

* * * * *